United States Patent
Ferretti et al.

(10) Patent No.: US 12,278,000 B2
(45) Date of Patent: Apr. 15, 2025

(54) METHOD FOR THE EARLY ESTIMATION OF ANAEROBIC DEGRADABILITY OF ORGANIC SUBSTRATES

(71) Applicant: POLITECNICO DI MILANO, Milan (IT)

(72) Inventors: Gianni Ferretti, Cremona (IT);
Arianna Catenacci, Milan (IT);
Francesca Maria Alessandra Malpei, Milan (IT)

(73) Assignee: POLITECNICO DI MILANO, Milan (IT)

( * ) Notice: Subject to any disclaimer, the term of this patent is extended or adjusted under 35 U.S.C. 154(b) by 231 days.

(21) Appl. No.: 17/785,284

(22) PCT Filed: Sep. 28, 2021

(86) PCT No.: PCT/IB2021/058848
§ 371 (c)(1),
(2) Date: Jun. 14, 2022

(87) PCT Pub. No.: WO2022/070035
PCT Pub. Date: Apr. 7, 2022

(65) Prior Publication Data
US 2023/0009939 A1    Jan. 12, 2023

(30) Foreign Application Priority Data

Sep. 30, 2020   (IT) .................. 102020000023089

(51) Int. Cl.
*G16C 20/10*   (2019.01)
*B09B 5/00*    (2006.01)
(Continued)

(52) U.S. Cl.
CPC .............. *G16C 20/10* (2019.02); *C02F 3/006* (2013.01); *G16C 20/70* (2019.02); *B09B 5/00* (2013.01); *C02F 3/30* (2013.01)

(58) Field of Classification Search
CPC ............. G16C 20/70; C02F 3/006; C02F 3/30
See application file for complete search history.

(56) References Cited

U.S. PATENT DOCUMENTS

2013/0130308 A1*   5/2013   Pautremat .......... G01N 33/1806
                                                              435/34

FOREIGN PATENT DOCUMENTS

| CN | 111044415 A | 4/2020 |
| CN | 111060477 A | 4/2020 |
| EP | 3205629 A1  | 8/2017 |

OTHER PUBLICATIONS

Da Silva C et al; "Biochemical methane potential (BMP) tests: Reducing test time by early parameter estimation"; Waste Management, New York; Oct. 21, 2017.
(Continued)

*Primary Examiner* — Lee E Rodak
*Assistant Examiner* — Sangkyung Lee
(74) *Attorney, Agent, or Firm* — Dickinson Wright PLLC; Andrew D. Dorisio

(57) ABSTRACT

A method for the early estimation of anaerobic degradability of organic substrates, starting from initial data acquired from tests measuring BMP (Biochemical Methane Potential). The method consists of: i) calculating the two parameters $B_0$ and k; ii) comparing the fit of the decreasing trend of $B_{0,est}$ as $\Delta t$ varies with a homographic function in the first quadrant; iii) evaluating the goodness of fit between a homographic function and the trend of $B_{0,est}$ as $\Delta t$ varies, checking whether the adjusted coefficient of determination $R^2_{adj} \geq R^2_{adj,min}$; iv) selecting the value of $B_{0,est}$ corresponding to a slope of less than 0.1% that occurs for three (Continued)

consecutive Δt; if no, acquire additional BMP measurements and repeat the previous steps.

10 Claims, 2 Drawing Sheets

(51) Int. Cl.
    *C02F 3/00*     (2023.01)
    *C02F 3/30*     (2023.01)
    *G16C 20/70*     (2019.01)

(56)     References Cited

OTHER PUBLICATIONS

Henrik Niemann et al; "A Simple Method for Estimation of Parameters in First Order Systems"; Journal of Physics; Dec. 16, 2014.

\* cited by examiner

METHOD FOR THE EARLY ESTIMATION OF ANAEROBIC DEGRADABILITY OF ORGANIC SUBSTRATES

TECHNICAL FIELD

The present invention relates to a method for the early estimation of anaerobic degradability of organic substrates, and in particular starting from initial data acquired from tests for measuring BMP (Biochemical Methane Potential).

BACKGROUND

In the field of renewable energy techniques usable for the production of biogas, waste organic substrates are used resulting from the management of municipal sewage and waste, as well as scrap/waste/by-products of agricultural or industrial origin.

The BMP (Biochemical Methane Potential) tests are recognised internationally, as well as nationally, a fundamental support not only for the selection of substrates and for the sizing of anaerobic digesters, but also for running and managing of the same, as well as for monitoring and optimising the process through mathematical modelling. In fact, the BMP test measures the maximum volume of methane that can be produced by a generic substrate under optimal process conditions. Despite the fact that the usefulness of BMP tests is undoubted, its duration (on average 30 days, but up to 100 days) makes large-scale application difficult, especially where, in practice, rapid response times are required to evaluate, and possibly take corrective action. Long testing times, in addition to resulting in high testing costs, are not always compatible, for utility plants and companies, with the timelines necessary for the specific case.

The BMP expresses the amount of methane that can be produced from the mass unit of the matrix (for example, in terms of Nl/kg SV, or $Nm^3/t$ SV, i.e., the gas volume at the reference conditions of 101.4 kPa and 0° C. per mass unit of volatile solids), under optimal digestion conditions.

To perform the test, batch reactors are used where the matrix, an inoculum of anaerobic microorganisms and the nutrients necessary for microbial metabolism are introduced and kept mixed and thermostated. Over time, the production of biogas and/or methane is measured volumetrically or manometrically, the evolution of which depends on the degradability properties of the matrix.

The documents CN111060477, EP3205629, and CN111044415 are known, which describe methods for the early estimation of anaerobic degradability of a substrate (BMP) starting from the measurement of some specific chemical and physical characteristics, by means of near-infrared spectroscopy (NIR) acquisition or by means of laser analysis of the size of the particles.

SUMMARY

The aim of the present invention is to provide a rapid method for the early estimation of anaerobic degradability of organic substrates (BMP), so as to shorten the times required for BMP tests.

Another aim is to provide a method that is simple to apply.

In accordance with the present invention, these aims and others still are achieved by a method for the early estimation of anaerobic degradability of organic substrates in accordance with claim 1.

Further characteristics of the invention are described in the dependent claims.

The advantages of this solution compared to solutions of the known art are various.

The use of a method of this type in data acquisition systems for BMP tests already on the market, would allow to shorten, by approximately 70% (as an average of the cases tested), the times necessary to obtain a reliable result with 95% probability. This would result in economic savings in terms of cost of testing, and a consequent more frequent use of the BMP tests for monitoring and controlling full-scale processes by utility plants and/or private companies.

This would also have a positive result in terms of management and optimization of the process of anaerobic digestion, making it possible, on the one hand, to undertake more rapid interventions should problems arise during the running of the plants, on the other hand, during the process optimization step, to achieve a better exploitation of the chemical energy contained in the treated organic substrates, with a higher production of biogas for same amount of mass of waste/scrap digested anaerobically.

The present invention concerns not only the application and optimization of this method to the specific case of anaerobic degradability tests, but also and above all the development of a procedure able to determine the time instant in which the number of acquired data is sufficient to guarantee a good prediction of the final BMP result. Starting from an experimental error (between replicates) of the BMP measurement considered acceptable when below 10%, the algorithm developed manages, in 95% of the cases tested, to estimate the final BMP with errors in the range of 1-13%, and using on average 30% of the time required for a BMP test (4-10 days). In relation to the dynamics of the experimental test, in 95% of the cases, the algorithm guarantees values of the statistical parameter rRMSE (square root of the mean square error, relative to the average of the observations) below 11% and $R^2_{adj}$ values (adjusted coefficient of determination) above 96%.

The method does not require the prior calibration of a statistical regression model that correlates the BMP with the chemical/physical analysis performed on the sample to be tested; moreover, it is not necessary to pre-treat the sample before performing the analysis, a process that can modify the degradability of a substrate; finally, there is no need to use specific instrumentation, which may not always be available at private companies or utility plants interested in an early prediction of the BMP: consequently, the algorithm proposed can be easily integrated into a data acquisition system for BMP tests, with reduced costs and ease of application.

BRIEF DESCRIPTION OF THE DRAWINGS

The features and advantages of the present invention will become clear from the following detailed description of a practical embodiment thereof, illustrated by way of non-limiting example in the accompanying drawings, in which.

DETAILED DESCRIPTION

Figure 1:
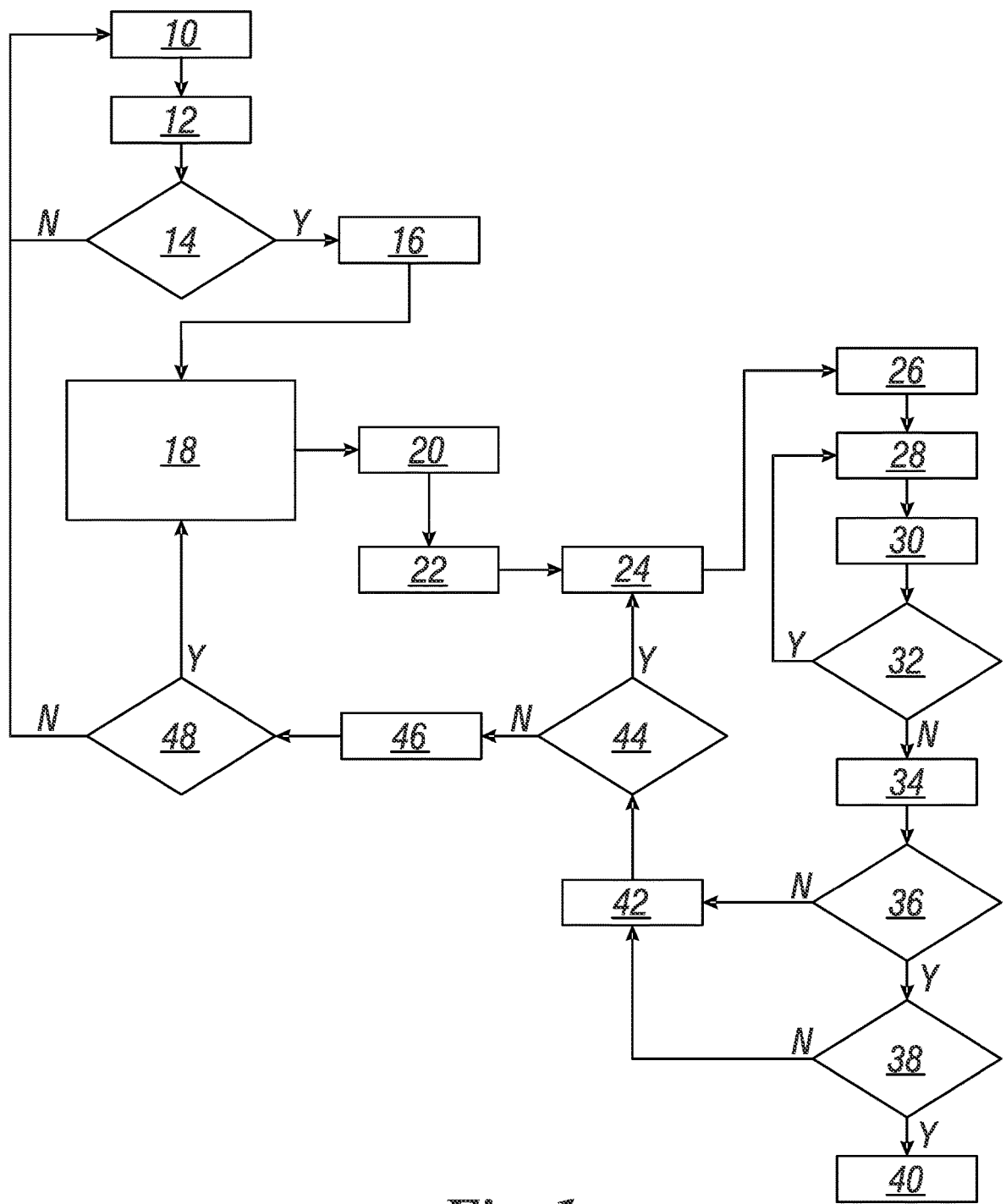
FIG. 1 shows a flowchart of a method for the early estimation of anaerobic degradability of organic substrates, in accordance with the present invention.
Figure 2:
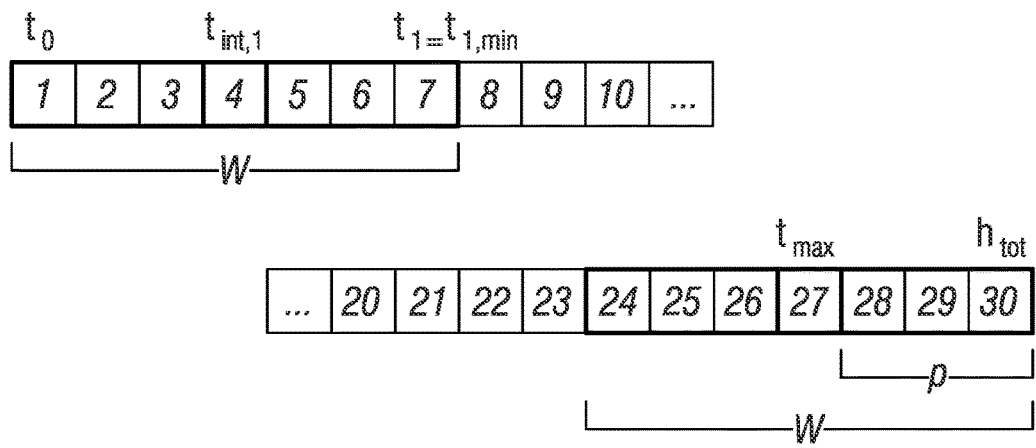
FIG. 2, in support of FIG. 1, shows how the two parameters $t_{min}$ and p, which are used for the early estimation of anaerobic degradability of organic substrates, are defined through an example provided for a generic data vector having a length equal to 30, in accordance with the present invention.

In accordance with the present invention, the method is based on the fact that, in a large number of real-world cases, the kinetics of substrate conversion to methane predominantly follows dynamics of the first order as can be seen in the following formula:

$$y(t) = B_0 \cdot (1 - e^{-k(t-t_0)})$$

where y(t) is the value of the signal at time t, $t_0$ is the test start time, $B_0$ is the maximum methane production at infinite time and k is the kinetic constant.

First order kinetics includes the cumulative effects of all the biochemical reactions that take place during the anaerobic degradation process, assuming the initial hydrolysis process as limiting. For this reason, and given its simplicity, which implies a limited number of parameters to be estimated, the dynamics of the first order remains the most widely used model to describe BMP curves.

In addition, a mathematical method proposed in the following article will be used to estimate the two parameters $B_0$ and k, from which it is possible to calculate the value of BMP at the end of the test.

Niemann, H. H., & Miklos, R. (2014). A Simple Method for Estimation of Parameters in First order Systems. Journal of Physics: Conference Series (Online), 570, [012001]. https://doi.org/10.1088/1742-6596/570/1/012001.

Assuming that a generic number m of test data is acquired, once a generic estimation time $t_1$ and a generic time interval $\Delta t$ (such that $\Delta t \leq m - t_1$) are defined, the procedure described by Niemann & Miklos estimates the first order kinetic parameters by using only part of the experimental data, and presuming that the prime derivative of the function at the time instant $t_1$ is known. This method, if applied to BMP tests, would allow to obtain very low estimation errors for specific values of $t_1$ and $\Delta t$, which, however, are not known a priori and must be appropriately selected to minimize the errors in the parameter estimations. In fact, due to the presence of noise in the experimentally acquired data, and dynamics that are not always attributable to a pure model of the first order, it is possible that, as the pairs $t_1$ and $\Delta t$ vary, the more or less significant estimation errors of the parameters $B_0$ and k alternate.

In the method developed it has been attempted to optimize the aspects considered most critical such as the removal of noise from the raw data acquired experimentally; the reliable estimation of the prime derivative of the curve at $t_1$; the identification of a method to select a given combination $t_1 - \Delta t$ at which the parameters $B_0$ and k are estimated early with an error that is considered acceptable.

The method developed allows, given a certain number of data acquired on an hourly basis from an experimental test, to select the pair of values $t_1 - \Delta t$ at which to estimate a final BMP value (derived from the parameters $B_0$ and k) which has a good probability of reducing the estimation error within values considered as acceptable. Through the method indicated, the kinetic parameters of the first order model are progressively calculated for each possible pair $t_1 - \Delta t$: when specific conditions are reached in the trend of the estimations of $B_0$ as $\Delta t$ varies, the method stops the iterations and returns the estimated BMP value.

The method comprises the following steps.

1). Acquire 12 and store a number of acquisitions every hour, $n_{data}$, of the measurements performed by an ongoing BMP test 10. A minimum number of data is required to start the algorithm ($n_{data,min}$). This number $n_{data,min}$ is defined, equal to at least 25, including the initial zero instant.

2). When the minimum number $n_{data,min}$ of measurements has been acquired, the condition that $n_{data} \geq n_{data,min}$ is checked 14. If yes Y, the calculation method starts, and the number of data $h_{tot}$ subsequently used for calculations is initialized 16 to $n_{data,min}$ ($h_{tot} = n_{data,min}$).

If no N, the acquisitions 12 of the performed BMP measurements 10 continue, and the number $n_{data}$ is incremented by one unit, step by step, until the pre-set total number of data $n_{data,min}$ is reached.

When $n_{data,min}$ is reached, storing stops (but data acquisition continues) and the variables $B_0$ and k (denoted by $B_{0,est}$ and $k_{est}$ where the suffix est stands for estimated value) are estimated early as will be seen in the next steps; $h_{tot}$ also represents the actual number of data used to obtain the estimation, correlated with the estimation time necessary for parameter prediction.

3). In order to remove the noise present in the acquired data 18 a moving average with a window W of length preferably equal to 7 samples (equivalent to 7 hours), is applied to the data. The new data vector will therefore have the same length as the original ($h_{tot}$); however, at the beginning and at the end of this vector, the reprocessed data cannot be considered reliable as the window W of the moving average is unbalanced at the extremes. For this reason, it is necessary to define two time indices in order to select the corresponding BMP data values, y(t), excluding the extremes of this vector.

A minimum value train, equal to 7, defined in order to properly calculate and average the value $y(t_{int,1})$, where the index $t_{int,1}$ is used to calculate the prime derivative at $t_1$, as will be further explained below.

A maximum index, $t_{max}$, calculated as the difference between $h_{tot}$ and p, where p is equal to 3 and takes into consideration the number of data that cannot be appropriately averaged when approaching the upper extreme of the vector of available data. It follows that with p=3, the last 7 values are averaged correctly.

4). It is therefore now possible to start calculating, for each possible pair $t_1 - \Delta t$, the early estimations of $B_0$ and k. In order to reduce the number of iterations to what is actually necessary with respect to subsequent processing, the maximum time index that can be assumed by $t_1$ (equal to $t_{1,max}$) is defined 20 as the difference between $t_{max}$ and $v(B_0)_{min}$, where $v(B_0)_{min} = 25$; it follows that $t_{1,max}$ is a function of only $t_{max}$ since $v(B_0)_{min}$ always remains constant, the latter being the minimum number of early estimations of $B_0$ necessary to decide whether or not to stop the iterations and then select the estimated parameters.

5). The generic index $t_1$ is initialized 22 at $t_{min}$.

6). Given the value of $t_1$, the maximum time interval $\Delta t_{max}$ to be considered is defined 24 as the difference between $t_{max}$ and $t_1$.

7). Subsequently, the generic time interval $\Delta t$ is initialized 26 at $t_1$, and $B_{0,est}$ and $k_{est}$ are calculated 28 based on the experimental values of methane produced measured at $t_1$ and at $(t_1 + \Delta t)$, and based on the value of the prime derivative of the experimental curve calculated at $t_1$. The calculation is performed as indicated in the article by Niemann & Miklos.

The method, allows the estimation of the first order kinetic parameters (k and $B_0$), once a part of the initial response of the system y(t) and its prime derivative y'(t) are known, given by the following equations:

$$y(t) = B_0 \cdot (1 - e^{-k(t-t_0)})$$

$$y'(t) = k \cdot B_0 \cdot e^{-k(t-t_0)}$$

where $t_0$ is the time instant in which the step function or initial step is applied to the system. The curves of y(t) and y'(t) can be seen in the graph on the left-hand side of FIG. 3.

Once a generic time instant $t_1$ and a generic time interval $\Delta t$ are defined, and assuming they are known:
- the values of the response signal of the system at $t_1$ and at $t_1 + \Delta t$, defined as $y(t_1)$ and $y(t_1 + \Delta t)$, respectively;
- the value of the prime derivative at $t_1$, defined as $y'(t_1)$;

it is possible to derive the following equation that allows to evaluate the constant k by solving the aforementioned equation for k:

$$R_1(\Delta t) = \frac{y(t_1 + \Delta t) - y(t_1)}{y'(t_1) \cdot \Delta t} = \frac{1 - e^{-k \cdot \Delta t}}{k \cdot \Delta t} = \frac{1 - e^{-\alpha}}{\alpha} = R(\alpha)$$

Figure 3:
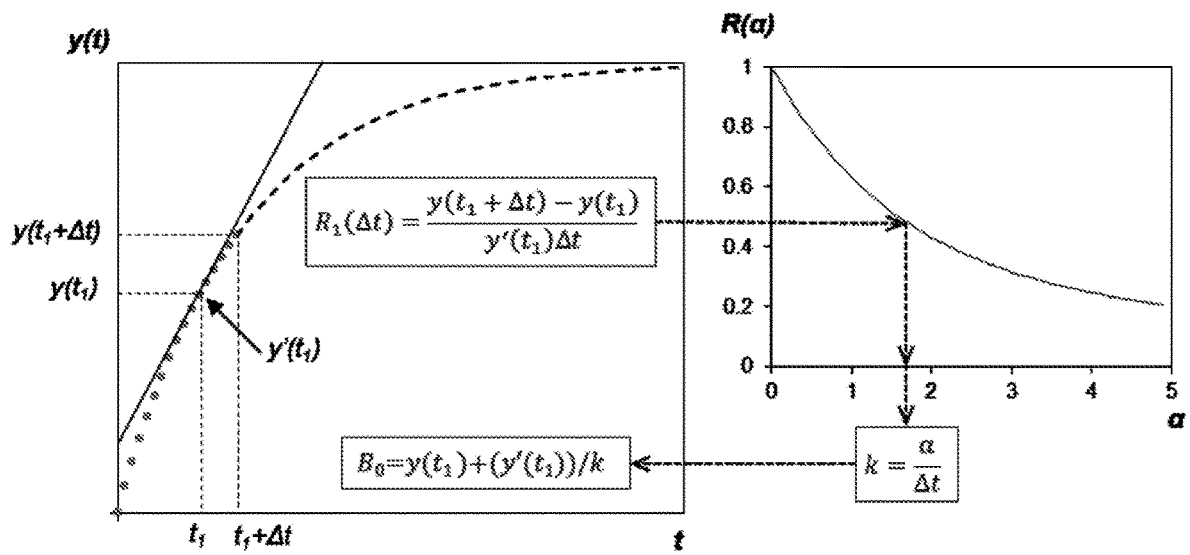
FIG. 3 shows graphs representing the calculation as set forth in the article by Niemann & Miklos, in accordance with the present invention.

Therefore, the calculation of $R_1(\Delta t)$ is performed with the data found in the graph on the left-hand side of FIG. 3, and k is represented by the graph on the right-hand side of FIG. 3, where $\alpha$ is in turn the product between the kinetic constant k (unknown) and the time interval $\Delta t$ adopted (known). As the value of $R_1(\Delta t)$ is known, it is in fact univocally possible to estimate the value of $\alpha$, by solving the following equation for $\alpha$:

$$R_1(\Delta t) - R(\alpha) = 0$$

Instead, the constant $B_0$ is calculated as shown in the following equation:

$$B_0 = y(t_1) + y'(t_1)/k$$

The prime derivative of the experimental curve calculated at $t_1$, is the result of the average between two values of prime derivative at $t_1$, calculated: in the first case starting from a prime derivative at $t_1$ of a spline evaluated in the points $t_{int,1}$–$t_1$–$t_{int,2}$; in the second case, starting from a prime derivative at $t_1$ of a spline evaluated in the points $t_1$–$t_{int,2}$–t. Where t is equal to the sum of $t_1$ and $\Delta t$, and $t_{int,1}$ and $t_{int,2}$ are the intermediate points between $t_0$–$t_1$ and $t_1$–t, respectively.

8). The time interval $\Delta t$ is then incremented by one time unit (one hour) 30, and calculation 28 of $B_{0,est}$ and $k_{est}$ is repeated 32 until $\Delta t$ reaches $\Delta t_{max}$.

9). To stop the calculation and select the parameters $B_0$ and k, it is necessary to check 34 the fitting to a homographic function in the first quadrant, of the decreasing trend of the curve of $B_{0,est}$ as $\Delta t$ varies.

A homographic function is a generic function having the following equation:

$$y = \frac{a \cdot x + b}{c \cdot x + d}$$

where the parameters a, b, c, d are estimated by nonlinear least squares regression techniques. In the present case, the Levenberg-Marquardt algorithm was used.

It has in fact been observed that, at a generic value of $t_1$, the trend of the curve of $B_{0,est}$ as a function of $\Delta t$ is similar to that of the estimation error of the parameter itself, and has a decreasing trend as explained. On the other hand, the estimations of k and their errors do not always have the same trend or at least an easily identifiable trend: for this reason, selecting the correct estimation of k can be more complex.

10). It is checked whether the fit 36 is good between homographic function and trend of $B_{0,est}$ as $\Delta t$ varies, i.e., $R^2_{adj} \geq R^2_{adj,min}$ with $R^2_{adj,min} = 0.998$ and where $R^2_{adj}$ is the adjusted coefficient of determination, namely:

$$R^2_{adj} = \left[\frac{(1 - R^2) \cdot (n - 1)}{n - z - 1}\right]$$

where $R^2$ is the coefficient of determination, n is the number of data available, and z is the number of independent variables of the regression.

If the fit 36 is not good, i.e., $R^2_{adj} < R^2_{adj,min}$, $t_1$ is incremented 42 by one unit and until 44 $t_1 \leq t_{1,max}$ the operations from 24 to 34 are performed.

It should be specified that the generic time interval $\Delta t$ is initialized at $t_1$ in order to remove the initial noise due to very small values of $\Delta t$.

11). It is checked 38 whether the function of $B_{0,est}$ has a slope of less than 0.1%, defined as $slope_{max} = 0.001$, i.e., that $slope \leq slope_{max}$ of the function $B_{0,est}$ that occurs for three consecutive $\Delta t$.

That is, the following conditions must hold simultaneously:

$$[B_{0,est(i)} - B_{0,est(i-1)}]/B_{0,est(i)} \leq slope_{max}$$

$$[B_{0,est(i-1)} - B_{0,est(i-2)}]/B_{0,est(i-1)} \leq slope_{max}$$

$$[B_{0,est(i-2)} - B_{0,est(i-3)}]/B_{0,est(i-2)} \leq slope_{max}$$

where index i identifies the progressive number of estimations of $B_{0,est}$ that have been calculated.

If yes, $B_{0,est}$ is selected 40 (as is the corresponding value of $k_{est}$) and the method stops and returns the result.

Otherwise, the value of tris incremented by one 42 and the operations from step 24 to step 34 are repeated.

12). If it is still not possible to select any value of $B_{0,est}$ and $k_{est}$, and 44 (N) $t_1 > t_{1,max}$, $h_{tot}$ is incremented 46 by one and, if 48 $h_{tot} \leq n_{data}$, step 18 and the subsequent steps are then performed, which are repeated until all the data acquired by the instrument are used ($n_{data}$), i.e., until 48 $h_{tot}$ is less than or equal to $n_{data}$. If no (N), and if no solution is found, this means that more data 10 are required before a reliable early estimation of the constants $B_0$ and k and therefore the BMP can be obtained.

In accordance with the present invention, it should be specified that the time necessary for the estimation does not depend upon the kinetic constant k; the time necessary for the estimation, and the goodness and reliability of the same, do not depend upon the type of substrate tested, nor upon the magnitude of the final BMP value found; the estimation errors of $B_0$ are less than or at least comparable with what has already been shown in the literature.

The method, as it is structured, can be easily integrated into a data acquisition software for BMP tests.

The method has been developed, and contextually optimized and checked, on multiple BMP test cases. To make this study more robust, note that these tests were conducted using different testing setup parameters (I/S ratio) and inoculum biomasses having different origins. In addition, the substrates tested are grouped into four different categories: primary sewage sludge, secondary sewage sludge, agricultural waste/scrap, foodstuff waste/scrap. Through the use of Akaike and Bayesian criteria, it was finally verified that the prevailing dynamics of the experimental curve of each of the BMP cases selected was a first order kinetics.

The method thus conceived is susceptible to numerous modifications and variations, all falling within the inventive concept; furthermore, all the details can be replaced by technically equivalent elements.

The invention claimed is:

1. A method for the early estimation of anaerobic degradability of organic substrate, returning an estimate of a final BMP value, wherein a BMP value expresses an amount of methane that can be produced from a unit mass of the organic substrate, comprising the following steps:

starting a BMP test, wherein the BMP test is carried out in a batch reactor where the organic substrate, an inoculum of anaerobic microorganisms, and nutrients necessary for microbial metabolism are introduced and kept mixed and thermostated;

acquiring and storing a minimum pre-set number of data from the BMP test;

considering that the anaerobic degradability of organic substrates follows the following formula:

$$Y(t)=B_0(1-e^{-k(t-t_0)})$$

where Y (t) is the value of the signal at time t, $B_0$ is the maximum production of methane at infinite time, k is the first-order kinetic constant; $t_0$ is the time at which acquisition of the data begins;

calculating parameters $B_0$ and k, subsequently identified as $B_{0,est}$ and $k_{est}$, for the pair $(t_1+\Delta t)$, where $t_1$ is a generic test time instant and $\Delta t$ is a generic time interval, incrementing the generic time interval $\Delta t$, and repeating the calculation of $B_{0,est}$ and $k_{est}$ until $\Delta t$ reaches a pre-set value $\Delta t_{max}$;

comparing a fit of the decreasing trend of the curve of $B_{0,est}$ as a function of $\Delta t$ with a homographic function in the first quadrant;

evaluating whether the fit of the decreasing trend of the curve $B_{0,est}$ as a function of $\Delta t$ with the homographic function has an adjusted coefficient of determination $R^2_{adj}$ greater than or equal to a pre-set minimum coefficient of determination $R^2_{adj,min}$;

if yes, then selecting a result for $B_{0,est}$, wherein the result is the estimate of the final BMP value which can be used to more effectively monitoring and optimizing the anaerobic digestion process, enabling timely interventions if issues arise; and stopping BMP data acquisition and storing;

wherein selecting the result comprises analysing the curve of $B_{0,est}$ as a function of $\Delta t$, and selecting a value of $B_{0,est}$ corresponding to a slope of the curve that is less than 0.1% for three consecutive $\Delta t$;

if no, acquire additional BMP measurements and repeat the previous steps; and using the result to manage and optimize a process of anaerobic digestion to enable intervention in the event of problems during running of a plant and to exploit chemical energy contained in treated organic substrates.

2. The method in accordance with claim 1 further comprising performing a moving average with a window W at said acquired data.

3. The method in accordance with claim 1 characterised in that the step of calculating the two parameters $B_0$ and k takes place by calculating the parameters $B_0$ and k, once a part of the initial response of the system y(t) and its prime derivative y'(t) are known, given by the following equations:

$$y(t)=B_0 \cdot (1-e^{-k \cdot (t-t_0)})$$

$$y'(t)=k \cdot B_0 \cdot e^{-k \cdot (t-t_0)}$$

where $t_0$ is the time instant in which the measurements are started.

4. The method in accordance with claim 3 characterised in that the step of calculating the two parameters $B_0$ and k comprises the step of calculating a first prime derivative of a spline calculated in first three predefined points.

5. The method in accordance with claim 3 characterised in that the step of calculating the two parameters $B_0$ and k comprises the step of calculating a second prime derivative of a spline calculated in second three predefined points.

6. The method in accordance with claim 4 characterised in that the step of calculating the two parameters $B_0$ and k comprises the step of calculating the average between said first derivative and said second derivative.

7. The method in accordance with claim 1 characterised in that said homographic function is a generic function having the following equation:

$$y = \frac{a \cdot x + b}{c \cdot x + d}$$

where the parameters a, b, c, d are estimated using nonlinear least squares regression techniques.

8. The method in accordance with claim 1 characterised in that said adjusted coefficient of determination $R^2_{adj}$ is given by the following equation:

$$R^2_{adj} = \left[ \frac{(1-R^2) \cdot (n-1)}{n-z-1} \right]$$

where $R^2$ is the coefficient of determination, n is the number of data available, and z is the number of independent variables of the regression.

9. The method in accordance with claim 1 characterised in that the step of selecting the value of $B_{0,est}$ corresponding to a slope of less than 0.1% that occurs for three consecutive $\Delta t$ comprises evaluating the following conditions:

$$[B_{0,est(i)}-B_{0,est(i-1)}]/B_{0,est(i)} \leq slope_{max}$$

$$[B_{0,est(i-1)}-B_{0,est(i-2)}]/B_{0,est(i-1)} \leq slope_{max}$$

$$[B_{0,est(i-2)}-B_{0,est(i-3)}]/B_{0,est(i-2)} \leq slope_{max}$$

where index i identifies the progressive number of estimations of $B_{0,est}$ that were calculated.

10. The method in accordance with claim 1 characterised in that the step of calculating the two parameters $B_0$ and k takes place for given values of $t_1$ and $\Delta t$, and where the generic time interval $\Delta t$ is initially initialized at $t_1$.

* * * * *